(12) United States Patent
Wang et al.

(10) Patent No.: US 9,342,902 B2
(45) Date of Patent: May 17, 2016

(54) METHOD AND APPARATUS FOR IMPROVING IMAGE RECONSTRUCTION SPEED

(71) Applicant: Shenyang Neusoft Medical Systems Co., Ltd., Shenyang (CN)

(72) Inventors: Hongbo Wang, Shenyang (CN); Shanshan Lou, Shenyang (CN)

(73) Assignee: SHENYANG NEUSOFT MEDICAL SYSTEMS CO., LTD., Shenyang (CN)

( * ) Notice: Subject to any disclaimer, the term of this patent is extended or adjusted under 35 U.S.C. 154(b) by 0 days.

(21) Appl. No.: 14/598,171

(22) Filed: Jan. 15, 2015

(65) Prior Publication Data

US 2016/0042536 A1 Feb. 11, 2016

(30) Foreign Application Priority Data

Aug. 11, 2014 (CN) .......................... 2014 1 0392380

(51) Int. Cl.
| | |
|---|---|
| *G06K 9/00* | (2006.01) |
| *A61B 6/00* | (2006.01) |
| *G06T 11/00* | (2006.01) |
| *A61B 6/03* | (2006.01) |
| *G06T 1/20* | (2006.01) |

(52) U.S. Cl.
CPC .............. *G06T 11/003* (2013.01); *A61B 6/032* (2013.01); *A61B 6/5205* (2013.01); *G06T 1/20* (2013.01)

(58) Field of Classification Search
CPC ............. G06K 9/00; A61B 5/00; G06T 11/00
USPC .............. 382/128–134; 378/4, 8, 21–27, 101, 378/901
See application file for complete search history.

(56) References Cited

U.S. PATENT DOCUMENTS

| | | | |
|---|---|---|---|
| 6,574,300 B1 * | 6/2003 | Florent ................... | G06T 5/002 378/19 |
| 6,907,099 B2 * | 6/2005 | Kling ........................ | G06T 1/20 378/4 |
| 2013/0188196 A1 * | 7/2013 | Kang ................. | G01B 9/02091 356/479 |

* cited by examiner

*Primary Examiner* — Abolfazl Tabatabai
(74) *Attorney, Agent, or Firm* — Kilpatrick Townsend & Stockton LLP (57) ABSTRACT

Disclosed are a method and apparatus for improving image reconstruction speed, to improve the image reconstruction speed by acquiring optimal thread configurations of execution units under different scanning conditions. The method includes: acquiring scanning data and extracting an image-construction parameter from the scanning data; generating thread configurations each comprising the numbers of threads in respective image reconstruction execution units, and obtaining image reconstruction speeds corresponding to the thread configurations by performing image reconstruction on the scanning data with the thread configurations; and obtaining image reconstruction speeds meeting a preset condition, grouping the thread configurations, which correspond to the image reconstruction speeds meeting the preset condition, into a candidate set, and extracting a thread configuration from the candidate set as an optimal thread configuration to be used in image reconstruction of the scanning data having the image-construction parameter.

16 Claims, 4 Drawing Sheets

METHOD AND APPARATUS FOR IMPROVING IMAGE RECONSTRUCTION SPEED

CROSS REFERENCE TO RELATED APPLICATION

This application claims the benefit of priority to Chinese Patent Application No. 201410392380.8, entitled "METHOD AND APPARATUS FOR IMPROVING IMAGE RECONSTRUCTION SPEED", filed on Aug. 11, 2014 with State Intellectual Property Office of PRC, which is incorporated herein by reference in its entirety.

FIELD

The present disclosure relates to the technical field of image processing, and in particular to a method and apparatus for improving image reconstruction speed.

BACKGROUND

In image reconstruction based on Computed Tomography (CT) data, a CT image reconstruction system is required to have a high image reconstruction speed due to a requirement of real-time capability. The image reconstruction speed generally refers to the number of images reconstructed per second.

A pipelining technology is often employed in the CT image reconstruction. Multiple steps involved in the image reconstruction are executed in parallel as a pipeline. For example, several steps such as data reading, correction, back-projection and post-processing involved in the tomography image reconstruction are executed in parallel as a pipeline. In order to improve a system operating speed, respective execution units may also operate in a multi-thread mode. In general, the more the threads in one execution unit for implementing a task are, the shorter the time consumed for executing the task is. However, the number of threads executed in parallel in one execution unit is limited due to a limitation of hardware resources (such as a CPU, a memory and a graphics card).

In the conventional technologies, the numbers of threads in the execution units are generally configured beforehand for performing image reconstruction. However, since the CT system has different scanning and image-construction parameters and time needed for the execution of the image-construction execution units varies under different scanning and image-construction parameters, it is impossible to achieve fastest image reconstruction speed under different scanning and image-construction parameters with fixed number of threads configured beforehand.

SUMMARY

In view of the above, the present disclosure provides a method and apparatus for improving image reconstruction speed, to solve the problem in the conventional technologies that it is impossible to achieve fastest image reconstruction speed adaptively under different scanning and image-construction parameters with fixed number of threads configured beforehand.

In order to solve the above problem, the present disclosure provides a technical solution as follows.

A method for improving image reconstruction speed is provided, which includes:

acquiring scanning data and extracting an image-construction parameter from the scanning data;

generating thread configurations each including the numbers of threads in respective image reconstruction execution units, and obtaining image reconstruction speeds corresponding to the thread configurations by performing image reconstruction on the scanning data with the thread configurations; and obtaining image reconstruction speeds meeting a preset condition, grouping the thread configurations corresponding to the image reconstruction speeds meeting the present condition into a candidate set, and extracting a thread configuration from the candidate set as an optimal thread configuration to be used in image reconstruction of the scanning data having the image-construction parameter.

Accordingly, the generating the thread configurations may include:

determining whether it is the first time to generate the thread configurations;

generating the thread configurations based on initialization information, if it is the first time to generate the thread configurations; and if it is not the first time to generate the thread configurations, taking a thread configuration corresponding to a currently fastest image reconstruction speed as a current thread configuration and obtaining a set of candidate thread configurations as newly generated thread configurations by changing, within an allowable range, the numbers of threads for one or more image reconstruction execution units in the current thread configuration.

Accordingly, changing the numbers of threads for one or more image reconstruction execution units in the current thread configuration may include:

changing, in a preset neighborhood of the current thread configuration, the numbers of threads for one or more image reconstruction execution units in the current thread configuration.

Accordingly, the method may further include:

deleting thread configurations which have already been generated, among the candidate thread configurations, returning to change the numbers of threads for one or more image reconstruction execution units in the current thread configuration if all the candidate thread configurations are deleted; and determining the remaining thread configurations as the newly generated thread configurations if not all the candidate thread configurations are deleted.

Accordingly, obtaining the image reconstruction speeds meeting the preset condition may include:

reading the image reconstruction speed to form a current image reconstruction speed set;

determining whether image reconstruction speeds in the current image reconstruction speed set meet a first preset condition, wherein the first preset condition includes conditions that a difference between a maximum and a minimal among the image reconstruction speeds is within a first preset range, the number of image reconstruction speeds is within a second preset range, an average value of the image reconstruction speeds is within a third preset range and a variance of the image reconstruction speeds is within a fourth preset range;

determining the image reconstruction speeds in the current image reconstruction speed set to be image reconstruction speeds meeting the preset condition, if the image reconstruction speeds in the current image reconstruction speed set meet the first preset condition; and classifying the image reconstruction speeds in the current image reconstruction speed set with a clustering algorithm if the image reconstruction speeds in the current image reconstruction speed set do not meet the first preset condition, choosing image reconstruction speeds in a class of fastest speeds as the current image reconstruction speed set, and returning to determine whether image reconstruction speeds in the current image reconstruction speed set meet the first preset condition.

Accordingly, extracting a thread configuration from the candidate set as the optimal thread configuration may include:

calculating, from the candidate set, average values of the numbers of threads for respective image reconstruction execution units, and determining in the candidate set a thread configuration which has a minimal distance to the average values of the numbers of threads as the optimal thread configuration.

Accordingly, extracting a thread configuration from the candidate set as the optimal thread configuration may include:

determining in the candidate set, a thread configuration which has a minimum sum of distances to other thread configurations, as the optimal thread configuration.

An apparatus for improving image reconstruction speed is provided, which includes:

a first extraction unit, configured to acquire scanning data and extract an image-construction parameter from the scanning data;

a generation unit, configured to generate thread configurations, each including the numbers of threads in respective image reconstruction execution units;

an image reconstruction unit, configured to perform an image reconstruction on the scanning data by using the thread configurations;

a first obtaining unit, configured to obtain image reconstruction speeds corresponding to the thread configurations;

a second obtaining unit, configured to obtain image reconstruction speeds meeting a preset condition and group thread configurations, which correspond to the image reconstruction speeds meeting the preset condition, into a candidate set; and a second extraction unit, configured to extract a thread configuration from the candidate set as an fastest image reconstruction speed thread configuration to be used in image reconstruction of the scanning data having the image-construction parameter.

Accordingly, the generation unit may include:

a first determining sub-unit, configured to determine whether it is the first time to generate the thread configurations;

a first generation sub-unit, configured to generate the thread configurations based on initialization information if it is determined by the first determining sub-unit that it is the first time to generate the thread configurations;

a searching sub-unit, configured to obtain a thread configuration corresponding to a currently fastest image reconstruction speed as a current thread configuration if it is determined by the first determining sub-unit that it is not the first time to generate the thread configurations; and a changing sub-unit, configured to change, within an allowable range, the numbers of threads for one or more image reconstruction execution units in the current thread configuration, to obtain a set of candidate thread configurations as newly generated thread configurations.

Accordingly, the changing sub-unit may be configured to:

change, in a preset neighborhood of the current thread configuration, the numbers of threads for one or more image reconstruction execution units in the current thread configuration within the allowable range, to obtain a set of candidate thread configurations as newly generated thread configurations.

Accordingly, the generation unit may further include:

a deleting sub-unit, configured to delete thread configurations which have already been generated, among the candidate thread configurations;

a returning sub-unit, configured to return to the changing sub-unit to change the numbers of threads for one or more image reconstruction execution units in the current thread configuration if all the candidate thread configurations are deleted; and a first determination sub-unit, configured to determine the remaining thread configurations as the newly generated thread configurations if not all the candidate thread configurations are deleted.

Accordingly, the second obtaining unit may include:

a reading sub-unit, configured to read the image reconstruction speed to form a current image reconstruction speed set;

a second determining sub-unit, configured to determine whether image reconstruction speeds in the current image reconstruction speed set meet a first preset condition, wherein the first preset condition includes conditions that a difference between a maximum and a minimal among the image reconstruction speeds is within a first preset range, the number of image reconstruction speeds is within a second preset range, an average value of the image reconstruction speeds is within a third preset range and a variance of the image reconstruction speeds is within a fourth preset range;

a second determining sub-unit, configured to determine the image reconstruction speeds in the current image reconstruction speed set to be image reconstruction speeds meeting the preset condition if the second determining sub-unit determines that the image reconstruction speeds in the current image reconstruction speed set meet the first preset condition;

a clustering sub-unit, configured to, if the second determining sub-unit determines that the image reconstruction speeds in the current image reconstruction speed set do not meet the first preset condition, classify the image reconstruction speeds in the current image reconstruction speed set with a clustering algorithm, choose image reconstruction speeds in a class of fastest speeds as the current image reconstruction speed set, and return to the second determining sub-unit to determine whether image reconstruction speeds in the current image reconstruction speed set meet the first preset condition; and a grouping sub-unit, configured to group the thread configurations corresponding to the image reconstruction speeds meeting the preset condition into a candidate set.

Accordingly, the second extraction unit may include:

a first calculation sub-unit, configured to calculate, from the candidate set, average values of the numbers of threads for respective image reconstruction execution units; and a second calculation sub-unit, configured to determine in the candidate set a thread configuration which has a minimal distance to the average values of the numbers of threads as the optimal thread configuration.

Accordingly, the second extraction unit may include:

a third calculation sub-unit, configured to determine in the candidate set, a thread configuration which has a minimum sum of distances to other thread configurations, as the optimal thread configuration.

It can be seen from the above that embodiments of the present disclosure have advantages as follows.

In the embodiments of the present disclosure, the image reconstruction speeds under different thread configurations for the threads in respective image reconstruction execution units are acquired based on a set of given image-construction parameters, the optimal thread configuration under the image-construction parameters may be obtained by analyzing the image reconstruction speeds and the corresponding thread configurations, and fastest image reconstruction speed may be reached by performing the image reconstruction with the optimal thread configuration under the above given image-construction parameters. Therefore, the optimal thread configurations corresponding to various image-construction parameters may be acquired and the overall image reconstruction speed may be improved.

DETAILED DESCRIPTION

For better understanding of the purpose, features and advantages of the present disclosure, embodiments of the present disclosure will be described below in further detail in conjunction with the drawings and the preferred embodiments.

In view of the issue in the conventional technologies that it is impossible to bring a system hardware performance into full play and reach fastest image reconstruction speed under each set of image-construction conditions with a single set of fixed thread numbers for the execution units, a method and apparatus for improving image reconstruction speed are proposed according to embodiments of the present disclosure, in which an image-construction parameter is extracted from scanning data in advance, different thread configurations are generated, image reconstruction is performed for the scanning data by using different thread configurations to obtain image reconstruction speeds corresponding to the thread configurations, and the thread configuration with an fastest image reconstruction speed for the scanning data, i.e., the optimal thread configuration corresponding to the image-construction parameter, is obtained from analysis of the image reconstruction speeds and corresponding thread configurations. Hence, the obtained fastest image reconstruction speed thread configuration can be used directly in case of image reconstruction performed under the condition of the same image-construction parameter, so as to achieve the fastest image reconstruction speed.

Figure 1:
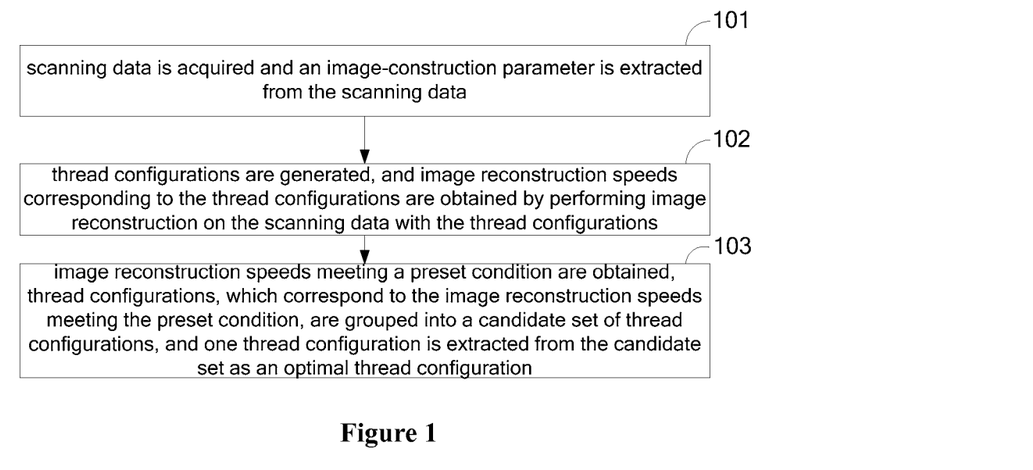
FIG. 1 is a flowchart of a method for improving image reconstruction speed according to a first embodiment of the present disclosure.

Based on the concept, referring to FIG. 1, a method for improving image reconstruction speed according to a first embodiment of the present disclosure may include steps 101 to 103 as follows.

In step 101, scanning data is acquired and an image-construction parameter is extracted from the scanning data.

The image-construction parameter may be interpreted as a parameter affecting image reconstruction speed, such as a pitch, an image-construction visual field, the thickness of image and an interval of image reconstruction. Since the image reconstruction speed and the parameter affecting the image reconstruction speed are generally in complicated non-linear relationship, particularly in the case that multiple factors affect the speed collectively, any image-construction parameter which has a large effect on the image reconstruction speed should be extracted.

The scanning data may be data obtained practically by scan, or may be test data of a production environment, simulated data, and the like.

In step 102, thread configurations, each including numbers of threads in respective image reconstruction execution units, are generated, and image reconstruction speeds corresponding to the thread configurations are obtained by performing image reconstruction on the scanning data with the thread configurations.

A main object of this step is to acquire the image reconstruction speeds under conditions of different thread configurations. The thread configuration includes the numbers of threads in respective image reconstruction execution units. Different image reconstruction execution units may be executed on one or more computers, in other words, resources which may be called by a thread in the image reconstruction execution unit according to the embodiment of the present disclosure may be program(s) running in one or more computers.

The image reconstruction speed may be calculated in the formula of: number of images per second (IPS)=the total number of images/a time interval from a start of the image-construction to the completion of the receipt for the last image. Specifically, whether the first one of the images should be counted in the total number of images and whether the time consumed in reconstructing the first one of the images should be included in the time interval from the start of the image-construction to the completion of the receipt for the last image may be set as needed; since the time consumed in reconstructing the first one of the images is generally long, the condition of considering the first one of the images or not should be kept the same in calculating the image reconstruction speeds with different thread configurations.

In step 103, image reconstruction speeds meeting a preset condition are obtained, thread configurations, which correspond to the image reconstruction speeds meeting the preset condition, are grouped into a candidate set of thread configurations, and one thread configuration is extracted from the candidate set as an optimal thread configuration to be used in image reconstruction of the scanning data having the image-construction parameter.

In view of noise and difference of practical execution conditions included in the result of the execution, stability of predicted thread configurations should be considered, i.e., to acquire most stable thread configuration under the same speed or condition. Therefore, multiple thread configurations corresponding to an image reconstruction speed meeting the preset condition, i.e., multiple thread configurations corresponding to a higher image reconstruction speed, should be obtained. Then a thread configuration which is more stable is chosen from the thread configurations as the optimal thread configuration corresponding to the above image-construction parameter condition. Optimal thread configurations under different image-construction parameters may be obtained by training with different scanning data and are stored in a database for being used in image construction.

A process for constructing an image with the optimal thread configuration is as follows. A practical image-construction parameter is extracted from practical scanning data after the practical scanning data needed for the image-construction is obtained. The practical image-construction parameter is compared with a trained image-construction parameter to obtain an image-construction parameter closest to the practical image-construction parameter. The comparison may be performed with schemes of minimum Euclidean distance, cosine similarity matching, and the like. Image construction is performed with the optimal thread configuration corresponding to the closest image-construction parameter, whereby the fastest image reconstruction speed may be achieved and hence the image reconstruction speed is improved.

Figure 2:
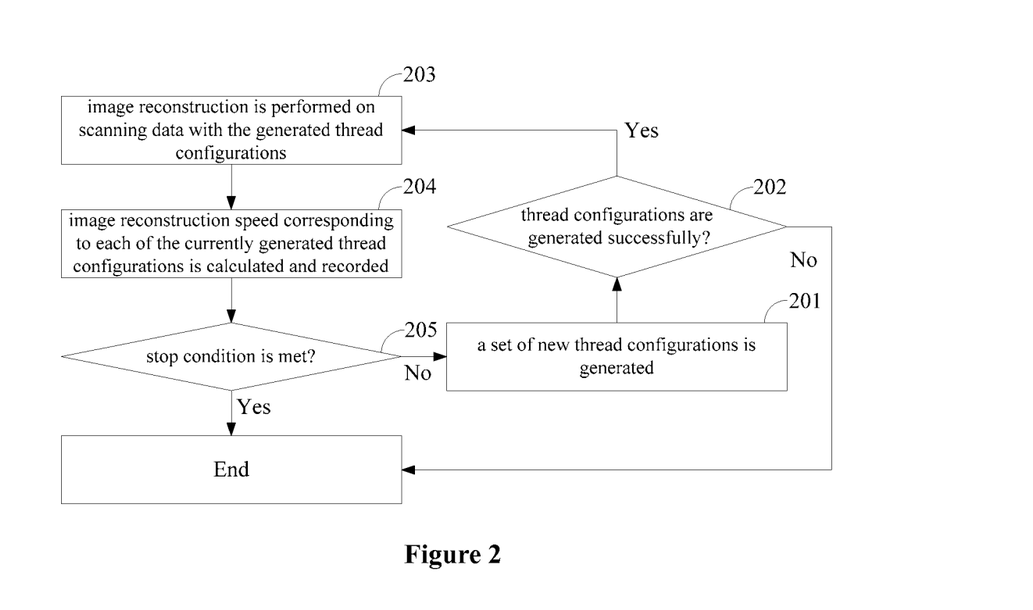
FIG. 2 is a flowchart of a method for improving image reconstruction speed according to a second embodiment of the present disclosure.

In some embodiments of the present disclosure, the process of generating the thread configurations and obtaining image reconstruction speeds corresponding to the thread configurations by performing image reconstruction on the scanning data with the thread configurations may be performed in a way of calculating and recording image reconstruction speeds whenever a group of thread configurations is generated and then returning to generate a new group of thread configurations until a stop condition is met. Referring to FIG. 2, which is a method for improving image reconstruction speed according to a second embodiment of the present disclosure, a process for obtaining image reconstruction speeds corresponding to different thread configurations is described.

In step 201: a set of new thread configurations is generated.

In step 202: it is determined whether the thread configurations are generated successfully; the process proceeds to step 203 if the thread configurations are generated successfully, and the process is ended if the thread configurations are not generated successfully.

In step 203, image reconstruction is performed on scanning data with the generated thread configurations.

In step 204, image reconstruction speed corresponding to each of the currently generated thread configurations is calculated and recorded.

In step 205, it is determined whether a stop condition is met; the process is ended if the stop condition is met, and the image reconstruction speeds corresponding to different thread configurations are obtained; and the process returns to step 201 if the stop condition is not met.

The stop condition generally may consist of the following elements that: (1) all possible thread configuration combinations have already been traversed; (2) the process has been executed for an amount of times exceeding a preset range; and (3) the process has been executed for a period exceeding a limitation.

In some embodiments of the present disclosure, an implementation for generating the thread configurations may include:

determining whether it is the first time to generate the thread configurations; generating the thread configuration based on initialization information if it is the first time to generate the thread configurations; and if it is not the first time to generate the thread configurations, taking a thread configuration corresponding to a currently fastest image reconstruction speed as a current thread configuration and obtaining a set of candidate thread configurations as newly generated thread configurations by changing, within an allowable range, the numbers of threads for one or more image reconstruction execution units in the current thread configuration.

In some embodiments of the present disclosure, an implementation for generating the thread configurations may further include:

deleting some thread configurations which have already been generated, among the candidate thread configurations; returning to change the numbers of threads for one or more image reconstruction execution units in the current thread configuration if all the candidate thread configurations are deleted; and determining the remaining thread configurations as the newly generated thread configurations if not all the candidate thread configurations are deleted.

Figure 3:
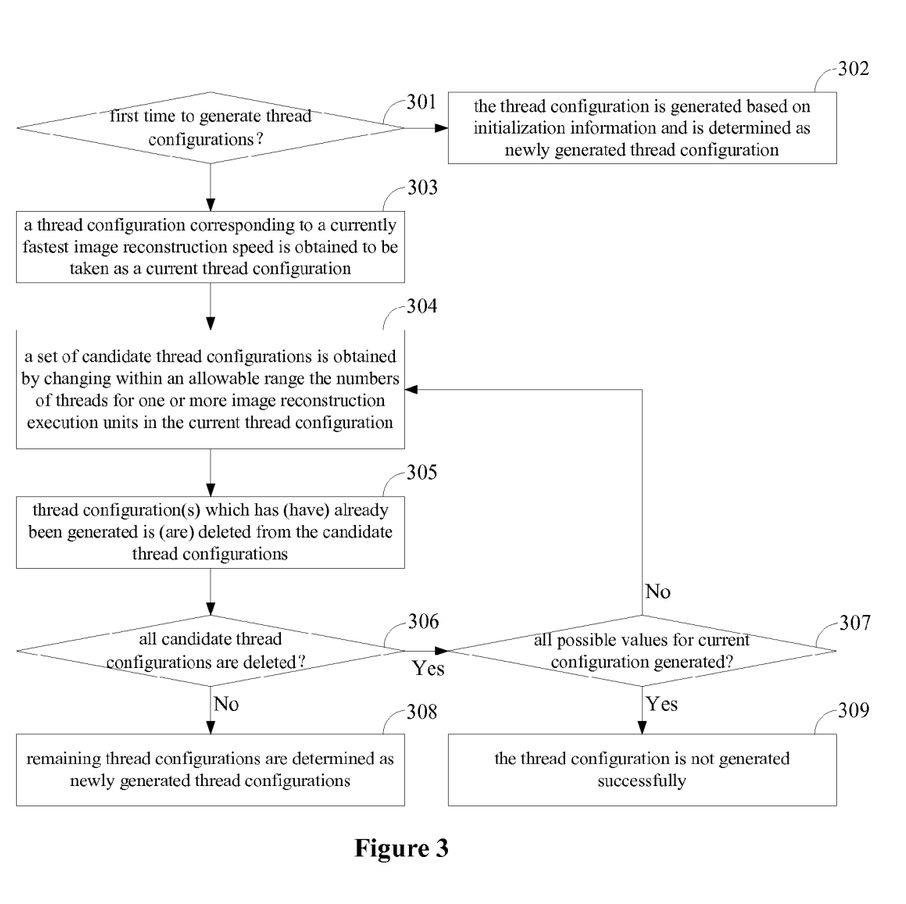
FIG. 3 is a flowchart of a method for improving image reconstruction speed according to a third embodiment of the present disclosure.

Referring to FIG. 3 showing a method for improving image reconstruction speed according to a third embodiment of the present disclosure, a process for generating the thread configurations (i.e. generating a set of new thread configurations) is described.

In step 301, it is determined whether it is the first time to generate the thread configurations; the process proceeds to step 302 if it is the first time to generate the thread configurations, and the process proceeds to step 303 if it is not the first time to generate the thread configuration.

In step 302, the thread configuration is generated based on initialization information and is determined as newly generated thread configuration.

The thread configuration generated for the first time may be a default configuration of a current system or a certain fixed value, for example, the numbers of threads in the image reconstruction execution units are each initialized as 1. The configuration may be made based on a ratio of durations needed for the execution of the threads, for example, assuming that the duration needed for the execution of a thread 1 is twice of the duration needed for the execution of a thread 2, then the number of the thread 1 may be set as twice of the number of the thread 2 in the initialization.

In step 303, a thread configuration corresponding to a currently fastest image reconstruction speed is obtained to be taken as a current thread configuration.

In step 304, a set of candidate thread configurations is obtained by changing within an allowable range the numbers of threads for one or more image reconstruction execution units in the current thread configuration.

In some embodiments of the present disclosure, changing in the current thread configuration the numbers of threads for one or more image reconstruction execution units may include: changing, within a preset neighborhood of the current thread configuration, the numbers of threads for one or more image reconstruction execution units in the current thread configuration.

A next set of thread configurations needs to be generated within a system allowable range, for example, within a range from a set minimum to a set maximum of the number of threads.

The next set of thread configurations may be chosen from a neighborhood with a distance L from the currently fastest thread configuration. The neighborhood with the distance L means that a sum of absolute values of variations of all thread configurations is L, for example, a variation of a first component is $L_1$, a variation of a second component is $L_2, \ldots$, and a condition of $L=L_1+L_2+\ldots+L_n$ is satisfied.

Assuming that the numbers of threads corresponding to the currently fastest thread configuration C are as shown in the following table:

|    | T1 | T2 | T3 | T4 | T5 | T6 |
|----|----|----|----|----|----|----|
| C1 | 3  | 4  | 5  | 7  | 4  | 6  |

If L=2 and for example T1 is to be changed, a variation of T1 may be +2 or −2, thus two corresponding sets of configurations are T1=5 or T1=1, and thread configurations as shown in the following table are generated:

|    | T1 | T2 | T3 | T4 | T5 | T6 |
|----|----|----|----|----|----|----|
| C1 | 5  | 4  | 5  | 7  | 4  | 6  |
| C1 | 1  | 4  | 5  | 7  | 4  | 6  |

Alternatively, T1 and T2 may be both changed, the variation of T1 may be +1 or −1, and a variation of T2 may also be +1 or −1, thereby thread configurations shown as the following table are generated:

|    | T1 | T2 | T3 | T4 | T5 | T6 |
|----|----|----|----|----|----|----|
| C1 | 4  | 5  | 5  | 7  | 4  | 6  |
| C1 | 4  | 3  | 5  | 7  | 4  | 6  |
| C1 | 2  | 5  | 5  | 7  | 4  | 6  |
| C1 | 2  | 3  | 5  | 7  | 4  | 6  |

In step 305, thread configuration(s) which has (have) already been generated is (are) deleted from the candidate thread configurations.

It is needed to delete the thread configuration(s) which has (have) already been generated before from the generated thread configurations, to avoid a repetition.

In step 306, it is determined whether all the candidate thread configurations are deleted, the process proceeds to step 307 if all the candidate thread configurations are deleted, and the process proceeds to step 308 if not all the candidate thread configurations are deleted.

In step 307, it is determined whether all possible values for the current thread configuration have been generated, the process proceeds to step 309 if all possible values for the current thread configuration have been generated, and the process returns to step 304 if not all possible values for the current thread configuration have been generated.

In the case that all the candidate thread configurations are deleted, it is needed to return and change the number of threads of one or more image reconstruction execution units in the current thread configuration to generate a set of new thread configurations. Re-changing the number of threads of one or more image reconstruction execution units in the current thread configuration may include: changing the number of threads of another one or more image reconstruction execution units; or, firstly enlarging the range of the neighborhood and changing within the enlarged neighborhood the number of threads of the image reconstruction execution unit(s) which was (were) changed last time, and if the number reaches an upper value of the neighborhood then changing the number of the threads of another one or more image reconstruction execution units until all the possible values for the current thread configuration have been generated.

In step 308, the remaining thread configurations are determined as newly generated thread configurations.

In step 309, the thread configuration is not generated successfully. If all the possible values of the current thread configuration have been generated, no new thread configuration can be generated successfully and the process is ended.

Furthermore, in generating the thread configurations, all possible thread configurations may be generated one by one, and the speed would be slower as compared with the speed in this embodiment of choosing new thread configurations from a neighborhood with a distance L from the currently fastest thread configuration.

In some embodiments of the present disclosure, obtaining the image reconstruction speeds meeting the preset condition may include:

reading the image reconstruction speeds to form a current image reconstruction speed set;

determining whether image reconstruction speeds in the current image reconstruction speed set meet a first preset condition, where the first preset condition includes conditions that a difference between a maximum and a minimum among the image reconstruction speeds is within a first preset range, the number of image reconstruction speeds is within a second preset range, an average value of the image reconstruction speeds is within a third preset range and a variance of the image reconstruction speeds is within a fourth preset range;

determining the image reconstruction speeds in the current image reconstruction speed set to be image reconstruction speeds meeting the preset condition if the image reconstruction speeds in the current image reconstruction speed set meet the first preset condition; and classifying the image reconstruction speeds in the current image reconstruction speed set with a clustering algorithm if the image reconstruction speeds in the current image reconstruction speed set do not meet the first preset condition, choosing image reconstruction speed from a class of fastest image reconstruction speeds as the current image reconstruction speed set, and returning to determine whether image reconstruction speeds in the current image reconstruction speed set meet the first preset condition.

Clustering the image reconstruction speeds to choose a candidate set specifically includes steps as follows.

1. An obtained image reconstruction speed set A is input.
2. It is determined whether the image reconstruction speed set A meets a classification standard which may include: whether a difference between a maximum and a minimum in the image reconstruction speed set A exceeds a given range; whether the number of elements in the image reconstruction speed set A is too large; and whether an average value and a variation for the image reconstruction speed set A is within a given range.

If the current image reconstruction speed set A meets the above requirement, the process jumps to step 4; otherwise, the process proceeds to step 3.

3. Classification is performed on the image reconstruction speed set A with a clustering algorithm to choose a set of fastest image reconstruction speeds to replace A, and the process jumps to step 2. The clustering algorithm may be a clustering algorithm such as k-means and k-medoids.
4. Thread configurations in the image reconstruction speed set A form the candidate set.

For example, the numbers T1, T2, . . . , T6 of threads in different thread configurations C1, C2, . . . , C8, and recorded image reconstruction speeds IPSs are shown in the following table.

After the image reconstruction speeds IPSs are clustered, a set of faster candidate thread configurations C1, C2, C3, C4, is obtained.

|    | T1 | T2 | T3 | T4 | T5 | T6 | IPS  |
|----|----|----|----|----|----|----|------|
| C1 | 3  | 4  | 5  | 7  | 4  | 6  | 24.5 |
| C2 | 3  | 5  | 6  | 3  | 2  | 6  | 23   |
| C3 | 4  | 5  | 6  | 8  | 3  | 6  | 22.7 |
| C4 | 4  | 5  | 6  | 3  | 2  | 6  | 22.3 |
| C5 | 4  | 6  | 6  | 8  | 2  | 6  | 18   |
| C6 | 6  | 5  | 5  | 6  | 3  | 5  | 17   |
| C7 | 4  | 5  | 5  | 5  | 4  | 6  | 14   |
| C8 | 3  | 7  | 6  | 3  | 3  | 6  | 13   |

Since only one thread configuration can be provided to be used in image reconstruction, it is needed to extract only one thread configuration from the candidate set as a final stable value. In some embodiments of the present disclosure, extracting one thread configuration from the candidate set as optimal thread configuration may be implemented in at least the following two ways.

1. Average values of the numbers of threads for respective image reconstruction execution units are calculated from the candidate set, and a thread configuration in the candidate set, which has a minimal distance to the average values of the numbers of threads is calculated as the optimal thread configuration. The distance in the embodiments of the present disclosure may be a Euclidean space distance, a Manhattan distance, and the like.

For example, referring to the following table, the average values of the numbers T1, T2, . . . , T6 of threads of the candidate set including C1, C2, C3, C4, are 3.25, 4.75, .75, 5.25, 2.75 and 6.

|  | T1 | T2 | T3 | T4 | T5 | T6 |
|---|---|---|---|---|---|---|
| C1 | 3 | 4 | 5 | 7 | 4 | 6 |
| C2 | 3 | 5 | 6 | 3 | 2 | 6 |
| C3 | 3 | 5 | 6 | 8 | 3 | 6 |
| C4 | 4 | 5 | 6 | 3 | 2 | 6 |
| average | 3.25 | 4.75 | 5.75 | 5.25 | 2.75 | 6 |

Then, it can be calculated that the configuration C2 among C1, C2, C3 and C4 is closest to the average values, since the Manhattan distance between C2 and the average values is:
|3−3.25|+|5−4.75|+|6−5.75|+|3−5.25|+|2−2.75|+|6−6|= 3.75. Hence, C2 is the optimal thread configuration.

2. A thread configuration in the candidate set, which has a minimum sum of distances to other thread configurations, is determined as the optimal thread configuration.

All optional thread configurations are traversed one by one, and the one which has a minimum sum of distances to other thread configurations, is determined as the final result. The distance in the embodiments of the present disclosure may be a Euclidean space distance, a Manhattan distance, and the like.

In this way, in the embodiments of the present disclosure, the image reconstruction speeds under different thread configurations for the threads in respective image reconstruction execution units are acquired based on a set of given image-construction parameters, the optimal thread configuration under the image-construction parameters may be obtained by analyzing the image reconstruction speeds and the corresponding thread configurations, and fastest image reconstruction speed may be reached by performing the image reconstruction with the optimal thread configuration under the above given image-construction parameters. Therefore, the optimal thread configurations corresponding to various image-construction parameters may be acquired and the overall image reconstruction speed may be improved.

That is to say, with the embodiments of the present disclosure, the image reconstruction speed may be improved by taking full advantage of the hardware performance without changing hardware resource configuration; the embodiments may be applicable in a wide range due to better adaptability to varying software or hardware resource, for example, with the method according to the embodiments of the present disclosure, an self-adaptive acceleration may be achieved even if the image reconstruction speed may be changed due to a replacement of a CPU or an image-construction card or a modification of a software algorithm, and a utilization ratio of the resource is optimized; and the embodiments have a high convenience because an optimization process is simplified and optimization becomes simple, and labor and time costs are saved since the optimization is performed by a computer instead of manually.

Figure 4:
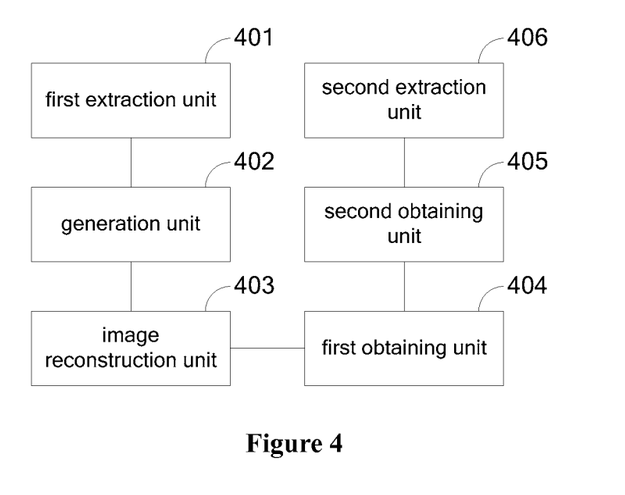
FIG. 4 is a schematic diagram of an apparatus for improving image reconstruction speed according to an embodiment of the present disclosure.

Accordingly, referring to FIG. 4, an apparatus for improving image reconstruction speed according to an embodiment of the present disclosure may include:

a first extraction unit 401, configured to acquire scanning data and extract an image-construction parameter from the scanning data;

a generation unit 402, configured to generate thread configurations, each including the numbers of threads in respective image reconstruction execution units;

an image reconstruction unit 403, configured to perform an image reconstruction on the scanning data by using the thread configurations;

a first obtaining unit 404, configured to obtain image reconstruction speeds corresponding to the thread configurations;

a second obtaining unit 405, configured to obtain image reconstruction speeds meeting a preset condition and group thread configurations, which correspond to the image reconstruction speeds meeting the preset condition, into a candidate set; and a second extraction unit 406, configured to extract a thread configuration from the candidate set as an optimal thread configuration to be used in image reconstruction of the scanning data having the image-construction parameter.

Figure 5:
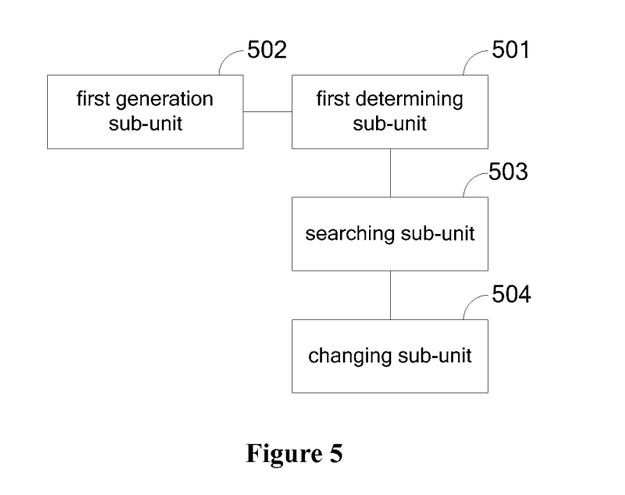
FIG. 5 is a schematic diagram of a generation unit according to an embodiment of the present disclosure.

Referring to FIG. 5, in some embodiments of the present disclosure, a first embodiment of the generation unit may include:

a first determining sub-unit 501, configured to determine whether it is the first time to generate the thread configurations;

a first generation sub-unit 502, configured to generate the thread configurations based on initialization information if it is determined by the first determining sub-unit that it is the first time to generate the thread configurations;

a searching sub-unit 503, configured to obtain a thread configuration corresponding to a currently fastest image reconstruction speed as a current thread configuration if it is determined by the first determining sub-unit that it is not the first time to generate the thread configurations; and a changing sub-unit 504, configured to change, within an allowable range, the numbers of threads for one or more image reconstruction execution units in the current thread configuration to obtain a set of candidate thread configurations as newly generated thread configurations.

Figure 6:
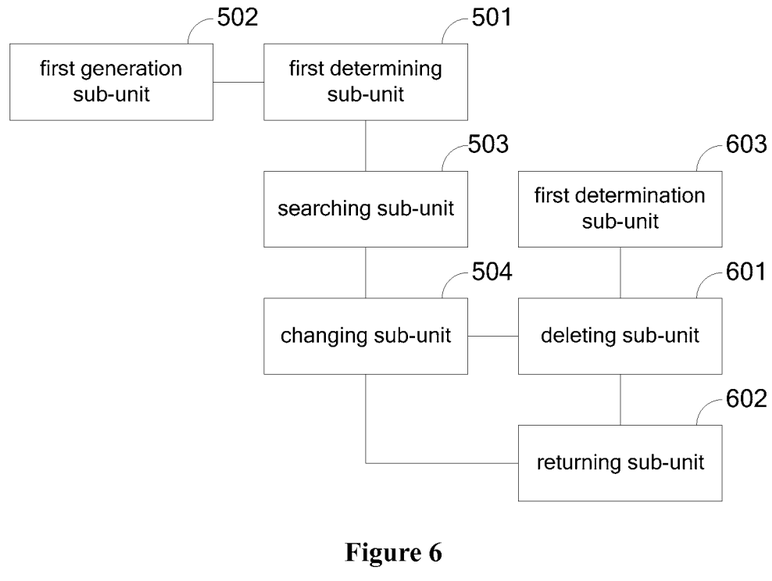
FIG. 6 is a schematic diagram of a generation unit according to another embodiment of the present disclosure.

Referring to FIG. 6, in some embodiment of the present disclosure, a second embodiment of the generation unit may include:

a first determining sub-unit 501, configured to determine whether it is the first time to generate the thread configurations;

a first generation sub-unit 502, configured to generate the thread configurations based on initialization information if it is determined by the first determining sub-unit that it is the first time to generate the thread configurations;

a searching sub-unit 503, configured to obtain a thread configuration corresponding to a currently fastest image reconstruction speed as a current thread configuration if it is determined by the first determining sub-unit that it is not the first time to generate the thread configurations;

a changing sub-unit 504, configured to change, within an allowable range, the numbers of threads for one or more image reconstruction execution units in the current thread configuration to obtain a set of candidate thread configurations as newly generated thread configurations;

a deleting sub-unit 601, configured to delete thread configurations which have already been generated, among the candidate thread configurations;

a returning sub-unit 602, configured to return to the changing sub-unit to change the numbers of threads for one or more image reconstruction execution units in the current thread configuration if all the candidate thread configurations are deleted; and a first determination sub-unit 603, configured to determine the remaining thread configurations as the newly generated thread configurations if not all the candidate thread configurations are deleted In some embodiment of the present disclosure, the changing sub-unit may be specifically configured to:

change, in a preset neighborhood of the current thread configuration, the numbers of threads for one or more image reconstruction execution units in the current thread configuration within the allowable range, to obtain a set of candidate thread configurations as newly generated thread configurations.

In some embodiments of the present disclosure, the second obtaining unit may include:

a reading sub-unit, configured to read the image reconstruction speed to form a current image reconstruction speed set;

a second determining sub-unit, configured to determine whether image reconstruction speeds in the current image reconstruction speed set meet a first preset condition, wherein the first preset condition includes that a difference between a maximum and a minimum among the image reconstruction speeds is within a first preset range, the number of image reconstruction speeds is within a second preset range, an average value of the image reconstruction speeds is within a third preset range and a variance of the image reconstruction speeds is within a fourth preset range;

a second determining sub-unit, configured to determine the image reconstruction speeds in the current image reconstruction speed set to be image reconstruction speeds meeting the preset condition if the second determining sub-unit determines that the image reconstruction speeds in the current image reconstruction speed set meet the first preset condition;

a clustering sub-unit, configured to, if the second determining sub-unit determines that the image reconstruction speeds in the current image reconstruction speed set do not meet the first preset condition, classify the image reconstruction speeds in the current image reconstruction speed set with a clustering algorithm, choose image reconstruction speeds in a class of fastest speeds as the current image reconstruction speed set, and return to the second determining sub-unit to determine whether image reconstruction speeds in the current image reconstruction speed set meet the first preset condition; and a grouping sub-unit, configured to group the thread configurations, which correspond to the image reconstruction speeds meeting the preset condition, into the candidate set.

In some embodiments of the present disclosure, the second extraction unit may include:

a first calculation sub-unit, configured to calculate, from the candidate set, average values of the numbers of threads for respective image reconstruction execution units; and a second calculation sub-unit, configured to determine in the candidate set a thread configuration which has a minimal distance to the average values of the numbers of threads as the optimal thread configuration.

In some embodiments of the present disclosure, the second extraction unit may include:

a third calculation sub-unit, configured to determine in the candidate set, a thread configuration which has a minimum sum of distances to other thread configurations, as the optimal thread configuration.

Therefore, in the embodiments of the present disclosure, the image reconstruction speeds under different thread configurations for the threads in respective image reconstruction execution units are acquired based on a set of given image-construction parameters, the optimal thread configuration under the image-construction parameters may be obtained by analyzing the image reconstruction speeds and the corresponding thread configurations, and fastest image reconstruction speed may be reached by performing the image reconstruction with the optimal thread configuration under the above given image-construction parameters. Therefore, the optimal thread configurations corresponding to various image-construction parameters may be acquired and the overall image reconstruction speed may be improved.

It should be noted that, the embodiments of the invention are described in a progressive way, each of which emphasizes the differences from others, and the same or similar elements among the embodiments can be referred to each other. Since the system or device disclosed in the embodiments corresponds to the method therein, the description thereof is relatively simple, and for relevant matters references may be made to the description of the method.

It should be noted that the relationship terminologies such as "first", "second" and the like are only used herein to distinguish one entity or operation from another, rather than to necessitate or imply that the actual relationship or order exists between the entities or operations. Furthermore, terms of "include", "comprise" or any other variants are intended to be non-exclusive. Therefore, a process, method, article or device including a plurality of elements includes not only the elements but also other elements that are not enumerated, or also include the elements inherent for the process, method, article or device. Unless expressively limited otherwise, the statement "comprising (including) one . . . " does not exclude the case that other similar elements may exist in the process, method, article or device.

The steps of the exemplary methods or algorithms can be implemented with hardware, software modules executed by a processor, or a combination thereof. The software modules may reside in a Random Access Memory (RAM), an internal memory, a Read Only Memory (ROM), an Electrically Programmable ROM, an Electrically-Erasable Programmable ROM, a register, a hard disk, a removable disk drive, CD-ROM, or other types of storage media well known in the field.

With the above descriptions of the disclosed embodiments, the skilled in the art may practice or use the present invention. Various modifications to the embodiments are apparent for the skilled in the art. The general principle suggested herein can be implemented in other embodiments without departing from the spirit or scope of the invention. Therefore, the present invention should not be limited to the embodiments disclosed herein, but has the widest scope that is conformity with the principle and the novel features disclosed herein.

The invention claimed is:

1. A method for improving image reconstruction speed, comprising:

acquiring scanning data and extracting an image-construction parameter from the scanning data;

generating thread configurations, each comprising information indicating the numbers of threads used for respective steps of image reconstruction, and obtaining image reconstruction speeds corresponding to the thread configurations by performing image reconstruction on the scanning data with the thread configurations; and obtaining image reconstruction speeds meeting a preset condition, grouping the thread configurations, which correspond to the image reconstruction speeds meeting the preset condition, into a candidate set of thread configurations, and extracting a thread configuration from the candidate set as an optimal thread configuration to be used in image reconstruction of the scanning data having the image-construction parameter.

2. The method according to claim 1, wherein generating the thread configurations comprises:

determining whether it is the first time to generate the thread configurations;

generating the thread configuration based on initialization information if it is the first time to generate the thread configurations; and if it is not the first time to generate the thread configurations, taking a thread configuration corresponding to a currently fastest image reconstruction speed as a current thread configuration and obtaining a set of candidate thread configurations as newly generated thread configurations by changing, within an allowable range, the numbers of threads for one or more steps of the image reconstruction in the current thread configuration.

3. The method according to claim 2, wherein changing the numbers of threads for one or more steps of the image reconstruction in the current thread configuration comprises:

changing, in a preset neighborhood of the current thread configuration, the numbers of threads for one or more steps of the image reconstruction in the current thread configuration.

4. The method according to claim 3, further comprising:

deleting thread configurations which have already been generated, among the candidate thread configurations, returning to change the numbers of threads for one or more steps of the image reconstruction in the current thread configuration if all the candidate thread configurations are deleted; and determining the remaining thread configurations as the newly generated thread configurations if not all the candidate thread configurations are deleted.

5. The method according to claim 2, further comprising:

deleting thread configurations which have already been generated, among the candidate thread configurations, returning to change the numbers of threads for one or more steps of the image reconstruction in the current thread configuration if all the candidate thread configurations are deleted; and determining the remaining thread configurations as the newly generated thread configurations if not all the candidate thread configurations are deleted.

6. The method according to claim 1, wherein obtaining the image reconstruction speeds meeting the preset condition comprises:

reading the image reconstruction speed to form a current image reconstruction speed set;

determining whether image reconstruction speeds in the current image reconstruction speed set meet a first preset condition, wherein the first preset condition comprises conditions that a difference between a maximum and a minimum among the image reconstruction speeds is within a first preset range, the number of image reconstruction speeds is within a second preset range, an average value of the image reconstruction speeds is within a third preset range and a variance of the image reconstruction speeds is within a fourth preset range;

determining the image reconstruction speeds in the current image reconstruction speed set to be image reconstruction speeds meeting the preset condition if the image reconstruction speeds in the current image reconstruction speed set meet the first preset condition; and classifying the image reconstruction speeds in the current image reconstruction speed set with a clustering algorithm if the image reconstruction speeds in the current image reconstruction speed set do not meet the first preset condition, choosing image reconstruction speeds in a class of fastest speeds as the current image reconstruction speed set, and returning to determine whether image reconstruction speeds in the current image reconstruction speed set meet the first preset condition.

7. The method according to claim 1, wherein extracting a thread configuration from the candidate set as the optimal thread configuration comprises:

calculating, from the candidate set, average values of the numbers of threads for respective steps of the image reconstruction, and determining in the candidate set a thread configuration which has a minimal distance to the average values of the numbers of threads as the optimal thread configuration.

8. The method according to claim 1, wherein extracting a thread configuration from the candidate set as the optimal thread configuration comprises:

determining in the candidate set, a thread configuration which has a minimum sum of distances to other thread configurations, as the optimal thread configuration.

9. An apparatus for improving image reconstruction speed, comprising:

one or more processors; and a memory having codes stored therein, when being executed by the one or more processors the codes configuring the one or more processors to:

acquire scanning data and extract an image-construction parameter from the scanning data;

generate thread configurations, each comprising information indicating the numbers of threads used for respective steps of image reconstruction;

perform an image reconstruction on the scanning data by using the thread configurations;

obtain image reconstruction speeds corresponding to the thread configurations;

obtain image reconstruction speeds meeting a preset condition and group thread configurations, which correspond to the image reconstruction speeds meeting the preset condition, into a candidate set; and extract a thread configuration from the candidate set as an optimal thread configuration to be used in image reconstruction of the scanning data having the image-construction parameter.

10. The apparatus according to claim 9, wherein when being executed by the one or more processors, the codes further configure the one or more processors to:

determine whether it is the first time to generate the thread configurations;

generate the thread configurations based on initialization information if it is determined that it is the first time to generate the thread configurations;

obtain a thread configuration corresponding to a currently fastest image reconstruction speed as a current thread configuration if it is determined that it is not the first time to generate the thread configurations; and change, within an allowable range, the numbers of threads for one or more steps of the image reconstruction in the current thread configuration, to obtain a set of candidate thread configurations as newly generated thread configurations.

11. The apparatus according to claim 10, wherein when being executed by the one or more processors, the codes further configure the one or more processors to:
change, in a preset neighborhood of the current thread configuration, the numbers of threads for one or more steps of the image reconstruction in the current thread configuration within the allowable range, to obtain a set of candidate thread configurations as newly generated thread configurations.

12. The apparatus according to claim 11, wherein when being executed by the one or more processors, the codes further configure the one or more processors to:
delete thread configurations which have already been generated, among the candidate thread configurations;
change the numbers of threads for one or more steps of the image reconstruction in the current thread configuration if all the candidate thread configurations are deleted; and
determine the remaining thread configurations as the newly generated thread configurations if not all the candidate thread configurations are deleted.

13. The apparatus according to claim 10, wherein when being executed by the one or more processors, the codes further configure the one or more processors to:
delete thread configurations which have already been generated, among the candidate thread configurations;
change the numbers of threads for one or more steps of the image reconstruction in the current thread configuration if all the candidate thread configurations are deleted; and
determine the remaining thread configurations as the newly generated thread configurations if not all the candidate thread configurations are deleted.

14. The apparatus according to claim 9, wherein when being executed by the one or more processors, the codes further configure the one or more processors to:
read the image reconstruction speed to form a current image reconstruction speed set;
determine whether image reconstruction speeds in the current image reconstruction speed set meet a first preset condition, wherein the first preset condition comprises conditions that a difference between a maximum and a minimum among the image reconstruction speeds is within a first preset range, the number of image reconstruction speeds is within a second preset range, an average value of the image reconstruction speeds is within a third preset range and a variance of the image reconstruction speeds is within a fourth preset range;
determine the image reconstruction speeds in the current image reconstruction speed set to be image reconstruction speeds meeting the preset condition if the image reconstruction speeds in the current image reconstruction speed set meet the first preset condition;
if the image reconstruction speeds in the current image reconstruction speed set do not meet the first preset condition, classify the image reconstruction speeds in the current image reconstruction speed set with a clustering algorithm, choose image reconstruction speeds in a class of fastest speeds as the current image reconstruction speed set, and determine whether image reconstruction speeds in the current image reconstruction speed set meet the first preset condition; and
group the thread configurations, which correspond to the image reconstruction speeds meeting the preset condition, into the candidate set.

15. The apparatus according to claim 9, wherein when being executed by the one or more processors, the codes further configure the one or more processors to:
calculate, from the candidate set, average values of the numbers of threads for respective steps of the image reconstruction; and
determine in the candidate set a thread configuration which has a minimal distance to the average values of the numbers of threads as the optimal thread configuration.

16. The apparatus according to claim 9, wherein when being executed by the one or more processors, the codes further configure the one or more processors to:
determine in the candidate set, a thread configuration which has a minimum sum of distances to other thread configurations, as the optimal thread configuration.

* * * * *